US006193986B1

(12) United States Patent
Sakurada

(10) Patent No.: US 6,193,986 B1
(45) Date of Patent: Feb. 27, 2001

(54) OILY COMPOSITION WITH INCREASED STABILITY AND PROCESS FOR PRODUCING THE SAME

(75) Inventor: Satoshi Sakurada, Yokosuka (JP)

(73) Assignee: The Nisshin Oil Mills, Ltd., Tokyo (JP)

( * ) Notice: Subject to any disclaimer, the term of this patent is extended or adjusted under 35 U.S.C. 154(b) by 0 days.

(21) Appl. No.: 09/028,952

(22) Filed: Feb. 24, 1998

(30) Foreign Application Priority Data

Feb. 25, 1997 (JP) ...................................... 9-040396
Aug. 15, 1997 (JP) ...................................... 9-220536

(51) Int. Cl.[7] .......................... A61K 9/10; A61K 9/107; A61K 9/00; A61K 6/00
(52) U.S. Cl. ......................... 424/401; 424/400; 514/165; 514/276; 514/775; 514/774; 514/474
(58) Field of Search ................................... 424/401, 400; 514/165, 276, 775, 774, 474

(56) References Cited

U.S. PATENT DOCUMENTS

| | | | |
|---|---|---|---|
| 4,107,343 | * | 8/1978 | Petricca . |
| 5,147,644 | * | 9/1992 | Oppenlaender et al. . |
| 5,948,926 | | 9/1999 | Takeo et al. . |

FOREIGN PATENT DOCUMENTS

| | | |
|---|---|---|
| 666300A2 | 8/1995 | (EP) . |
| 81 054 136 B | * 12/1981 | (JP) . |
| 63-135483 | 6/1988 | (JP) . |
| 3-205 466 | * 9/1991 | (JP) . |
| 4-64638 | 10/1992 | (JP) . |
| 5-049 909 | * 3/1993 | (JP) . |
| 6-343400 | 12/1994 | (JP) . |
| 7-258 682 | * 10/1995 | (JP) . |
| 9-157 179 | * 6/1997 | (JP) . |

OTHER PUBLICATIONS

Translation of Hei 9–157179, Jun. 1997.*

* cited by examiner

Primary Examiner—Thurman K. Page
Assistant Examiner—Brian K. Seidleck
(74) Attorney, Agent, or Firm—Burns, Doane, Swecker & Mathis, LLP

(57) ABSTRACT

An oily composition having excellent storability and forming no precipitate of an ingredient selected from the group of gelatin and gum arabic during the storage for a long period of time is provided. This composition is composed of a solid phase comprising an effective substance selected from the group consisting of a water-soluble substance and water-dispersible substance and 50 to 4,000 parts by weight, for 100 parts by weight of the effective substance, of the ingredient, and an oil phase comprising an oily component and an emulsifier, wherein the solid phase in the form of fine particles having an average particle diameter of not larger than 5 $\mu$m is dispersed in the oil phase, the water content of the solid phase is not higher than 30% by weight and the water content of the whole composition is not higher than 20% by weight.

21 Claims, No Drawings

OILY COMPOSITION WITH INCREASED STABILITY AND PROCESS FOR PRODUCING THE SAME

BACKGROUND OF THE INVENTION

The present invention relates to an oily composition and a process for producing it. In particular, the present invention relates to an oily composition excellent in storability and a process for producing it. The oily composition of the present invention is usable in the fields of foods, feeds, cosmetics, medicines, agricultural chemicals, machines and various industrial fields, taking advantage of excellent stability thereof.

An effective substance can be dispersed in an oil by directly adding the effective substance to the oil containing an emulsifier dissolved therein and mixing them. However, in this process, it is difficult to homogeneously disperse the effective substance in the oil phase to obtain a stable dispersion because this substance is immediately coagulated and precipitated. There is usually employed a process wherein an aqueous phase containing the effective substance dissolved therein is mixed with an oil phase to obtain a water-in-oil emulsion composition. The water-in-oil type emulsion compositions wherein the aqueous phase contains some substance, which were proposed hitherto, include a W/O-type emulsion containing an antioxidizing substance difficultly soluble in oils and fats and/or a synergist [Japanese Patent Publication for Opposition Purpose (hereinafter referred to as "J. P. KOKOKU") No. Hei 4-64638], a W/O-type lipophilic antioxidant prepared by emulsifying a water-soluble antioxidizing substance [Japanese Patent Unexamined Published Application (hereinafter referred to as "J. P. KOKAI" No. Sho 63-135483), a W/O-type emulsified composition containing an acid substance and/or a salt thereof (J. P. KOKAI No. Hei 6-343400), etc.

However, the purposes of using the above-described W/O type emulsified compositions in various fields were not completely attained because the aqueous phase is separated out or oiling off is caused during the storage by the influence of salts and acid substances contained in the aqueous phase even though no separation is caused immediately after the preparation of the compositions.

SUMMARY OF THE INVENTION

Therefore, an object of the present invention is to provide an oily composition having various advantages such as freeness from the precipitation of an effective substance in the course of the storage for a long period of time, an excellent storability, good masking of tastes, high thermal resistance, excellent controlling of dissolving out of water-soluble substances, high hygienic effect, exhibition of the antioxidizing function to an extent higher than that exhibited when the antioxidant is used as it is as the effective substance, and possibility of being used in combination with an oily antioxidant. Another object of the present invention is to provide a process for producing such an oily composition.

After intensive investigations, the inventors have found that the above-described objects of the present invention can be attained by an oily composition prepared by dispersing the effective substance in the form of a specified fine particles in an oil phase and limiting the water content of the solid phase and also the water content of the whole composition.

The present invention has been completed on the basis of the above-described finding. The present invention provides an oily composition composed of a solid phase comprising an effective substance selected from the group consisting of a water-soluble substance and water-dispersible substance and 50 to 4,000 parts by weight, for 100 parts by weight of the effective substance, of an ingredient selected from the group consisting of gelatin and gum arabic, and an oil phase comprising an oily component and an emulsifier, wherein the solid phase in the form of fine particles having an average particle diameter of not larger than 5 $\mu$m is dispersed in the oil phase, the water content of the solid phase is not higher than 30% by weight and the water content of the whole composition is not higher than 20% by weight.

The present invention also provides an oily composition composed of a solid phase comprising an effective substance selected from the group consisting of citric acid, common salt, sodium L-glutamate, sodium L-ascorbate, Aspirin, vitamin B., calcium chloride and casein calcium peptide, and 50 to 4,000 parts by weight, for 100 parts by weight of the effective substance, of an ingredient selected from the group consisting of gelatin and gum arabic, and an oil phase comprising an oily component selected from the group consisting of soybean oil, liquid paraffin, bees wax, squalane and fish oil, beef tallow, and an emulsifier, wherein the solid phase in the form of fine particles having an average particle diameter of 0.05 to 5 $\mu$m is dispersed in the oil phase, the water content of the solid phase is 0 to 30% by weight and the water content of the whole composition is 0 to 20% by weight.

The present invention also provides a process for producing an oily composition, which comprises heating an aqueous phase comprising an effective substance selected from the group consisting of a water-soluble substance and water-dispersible substance, an ingredient selected from the group consisting of gelatin and gum arabic and water to a dissolution temperature of the ingredient or higher, mixing the aqueous phase with an oil phase containing an oily component and an emulsifier to finally obtain a W/O-type emulsion and then dehydrating the emulsion to control the water content of the whole composition at 20% by weight or lower.

DESCRIPTION OF THE PREFERRED EMBODIMENTS

The detailed description will be made on the oily composition of the present invention.

The oily composition of the present invention is composed of a solid phase comprising an effective substance selected from the group consisting of a water-soluble substance and water-dispersible substance, and an ingredient selected from the group consisting of gelatin and gum arabic, and an oil phase comprising an oily component and an emulsifier.

Examples of the effective substances usable in the present invention include sour seasonings, antioxidants, enzymes, bacteria, seasonings, inorganic salts, starches, amylolysis products, peptides, amino acids, dietary fibers, celluloses, nutrients, medicines, antibiotics, vaccines, insulin, and animal and vegetable extracts. In particular, they include citric acid and salts thereof, phosphoric acid and salts thereof, metaphosphoric acid and salts thereof, phospholipase, amylase, dehydrogenase, lactic acid bacteria, butyric acid bacteria, common salt, soy sauce, sodium carbonate, corn starch, dextrin, milk peptide, corn peptide, L-tryptophane, lysine chloride, sodium glutamate, polydextrose, microcrystalline cellulose, ascorbic acid and salts thereof, nicotinamide, magnesium L-ascorbyl phosphate, vitamin B's, niacin, calcium pantothenate, folic acid, biotin, calcium salts such as calcium chloride, milk minerals, calcium lactate, casein, calcium caseinate peptides, calcium phosphopeptide (CPP), KARUSHIUMU SAITORETOMATO (CCM), beef bone meal, shell powder, heme iron, arbutin, kojic acid, dipotassium glycyrrhizate, chlorpheniramine maleate, codeine phosphate, Aspirin, influenza vaccine, gymnema sylvestre extract, royal jelly, propolis, RAKANKA extract, herb extracts, grape extract, blueberry extract, rosemary extract, tea extract, cowberry extract, etc. These effective substances are used either alone or in combination of two or more of them. The amount of the effective substance is preferably 0.1 to 80% by weight, more preferably 1 to 70% by weight, based on the whole solid phase of the oily composition.

The term "gelatin" herein indicates polypeptides obtained from collagen contained in a high concentration in bones and skins of animals by extraction followed by purification and chemical and enzymatic decomposition. Those used in the fields of foods, feeds, cosmetics, medicines and industries are usable without any special limitation. Purified gelatin obtained by bleaching, purification, etc. is also usable.

The gum arabic used in the present invention is one usually used in the fields of foods, feeds, cosmetics, medicines and industries.

The solid phase in the oily composition of the present invention may contain both gelatin and gum arabic or either of them.

The amount of the ingredient selected from the group consisting of gelatin and gum alabic in the solid phase is 50 to 4,000 parts by weight, preferably 80 to 2,000 parts by weight, for 100 parts by weight of the effective substance. The content of the ingredient in the solid phase is preferably 10 to 99% by weight.

If necessary, a hydrophilic sulfactant having an HLB of above 10 may be added to the solid phase of the oily composition of the present invention. HLB of the hydrophilic surfactant used is preferably not above 18. The hydrophilic surfactant having an HLB of above 10 include, for example, sucrose fatty acid esters, polyglycerol fatty acid esters, lysolecithin, saponin, glycolipids, proteins, proteolysis products (excluding gelatin), silicone surfactants and alkylene oxide adducts of surfactants. When a hydrophilic surfactant having an HLB higher than 10 is used, the amount thereof is preferably 0.01 to 3% by weight based on the whole oily composition.

A polyhydric alcohol usually used as a softener for gelatin can be added to the solid phase of the oily composition of the present invention, if necessary. Although various polyhydric alcohols are usable, water-soluble polyhydric alcohols having at least 2, preferably 2 to 12, and more preferably 2 to 6 hydroxyl groups in the molecule are preferred. Examples of such polyhydric alcohols include glucose, maltose, maltitol, sorbitan, sorbitol, sucrose, fructose, xylitol, inositol, erythritol, pentaerythritol, propylene glycol, 1,3-butylene glycol, ethylene glycol, glycerol, diglycerol, triglycerol, polyglycerols (average degree of polymerization: 4 to 10), reducing starch saccharide, glucose/fructose liquid sugar and fructose/glucose liquid sugar. The polyhydric alcohols are usable either alone or in combination of two or more of them. Further, thickening polysaccharides other than gum arabic can be added to the solid phase of the oily composition of the present invention, if necessary. The thickening polysaccharides include, for example, xanthane gum, guar gum, locust bean gum, carrageenan, agar, pectin, sodium alginate, Gellan gum, carboxymethylcellulose and methylcellulose. The thickening agents are usable either alone or in combination of two or more of them.

The solid phase of the oily composition of the present invention may further contain well-known additives such as antiseptics, colorants, flavors and pH regulators.

When the polyhydric alcohol, thickening polysaccharide or additive is added, the amount of the polyhydric alcohol is preferably 0.1 to 40% by weight and that of the thickening polysaccharide is preferably 0.01 to 5% by weight based on the whole solid phase of the oily composition.

The solid phase of the oily composition of the present invention has a water content of not higher than 30% by weight, preferably 0 to 20% by weight and more preferably 0 to 15% by weight. The method for controlling the water content of the solid phase of the oily composition of the present invention at not higher than 30% by weight is not particularly limited and it may be, for example, vacuum drying method, heat drying method, film distillation drying method or freeze-drying method.

The solid phase of the oily composition of the present invention comprises fine particles having an average diameter of not longer than 5 $\mu$m, which are dispersed in the oil phase which will be described below. The average diameter of the particles in the solid phase is preferably 0.05 to 3 $\mu$m. The method for making the solid phase, which is dispersed in the oil phase, fine particles having an average diameter of not longer than 5 $\mu$m is not particularly limited. Such fine particles can be obtained, for example, by slowly mixing the oil phase with the aqueous phase with a homomixer for about 30 minutes to obtain an emulsion or by finally obtaining a W/O-type emulsion with an emulsifying machine such as a high-pressure homogenizer or microfluidizer and dehydrating the emulsion with an oil pump or the like under reduced pressure. The expression "to finally obtain a W/O-type emulsion" herein indicates that even when the emulsion is of O/W-type or a mixture of O/W-type and W/O-type in the emulsification step, the emulsion should be of W/O-type finally.

The average particle diameter in the solid phase is a value determined by measuring with a particle size distribution meter of laser diffraction type (type LA-500; a product of Horiba, Ltd.).

The description will be made on the oil phase of the oily composition of the present invention. The oil phase comprises an emulsifier and an oily component. The emulsifiers are not particularly limited and any of known emulsifiers used in the fields of foods, feeds, cosmetics, medicines, industries, etc. are usable. The emulsifiers preferably used in the present invention are surfactants having an HLB of not higher than 10. HLB of the surfactants is preferably at least 1.

The surfactants having an HLB of not higher than 10 include, for example, sorbitan fatty acid esters, glycerol fatty acid esters, organic acid monoglycerides, propylene glycol fatty acid esters, diglycerides, sucrose fatty acid esters, polyglycerol fatty acid esters, lecithins, silicone surfactants and alkylene oxide adducts of surfactants. In particular, they include sorbitan monooleate, sorbitan distearate, polyoxyethylene (6 mol) sorbitan monostearate, ghlycerol monostearate, glycerol monolinolate, esters of citric acid and glycerol, propylene glycol monostearate, glycerol dioleate, glycerol dilinolate, diglycerides obtained by the transesterification of rape seed oil and glycerol, diglycerides obtained by the transesterification of safflower and glycerol, diglycerol distearate, diglycerol tristearate, hexaglycerol trioleate, hexaglycerol pentastearate, tetraglycerol-condensed licinolate, polyglycerol-condended licinoleic acid ester, sucrose tri- to penta-stearates, polyoxyethylene (5 mol) cetyl ether, polyoxyethylene (3 mol) nonyl phenyl ether, polyoxyethylene (6 mol) stearyl ether, polyoxyethylene (5 mol) hardened castor oil, polyoxyethylene (15 mol) hardened castor oil, polyoxyethylene (20 mol) sorbitol tetraoleate, lecithin (Lecithin DX, BASIS LP-20; products of The Nisshin Oil Mills, Ltd.) and dimethylsiloxane/methyl (polyoxyethylene 5 mol adduct)siloxane copolymer.

The surfactant having an HLB of not higher than 10 can be used in combination with an emulsifier having an HLB of 10 or above in the present invention. Such emulsifiers include, for example, sucrose fatty acid esters, polyglycerol fatty acid esters, lysolecithins, saponin, glycolipids, proteins, proteolysis products (excluding gelatin), silicone surfactants and alkylene oxide adduct surfactants. In particular, they include sucrose monostearate, hexaglycerol monooleate, decaglycerol monostearate, enzymatic decomposition products of lecithin (BASIS LG-10K and BASIS LP-20E; products of The Nisshin Oil Mills, Ltd.), quillaia saponin, decomposition products of soybean proteins, sodium caseinate, dimethylsiloxane/methyl(60 mol polyoxyethylene adduct)siloxane copolymers, castor oil hardened with polyoxyethylene (25 mols) and castor oil hardened with polyoxyethylene (80 mols). It is particularly desirable in the present invention to use the polyglycerol condensed ricinoleate or a combination thereof with a polyglycerol fatty acid ester, a glycerol monofatty acid ester or lecithin.

The above-described emulsifiers may be used either alone or in combination of two or more of them.

As the oily component, any of known oily components used in the fields of foods, feeds, cosmetics, medicines and industries can be used without any particular limitation. The oily components used are in a liquid form. Particularly, they may be also those which are in liquid form at ambient temperature or those which are molten by heating. The oily components include, for example, hydrocarbons, esters, animal and vegetable oils and fats, waxes, higher fatty acids, higher alcohols, silicones, sterols and resins, as well as those obtained by an enzymatic treatment (hydrolysis or transesterification, etc.) or chemical treatment (transesterification, hydrogenation, etc.) of them. From the viewpoints of the easiness of the preparation and handling, the oily components which are in liquid form or which have a fluidity at ambient temperature are preferred.

The oily components which are in liquid form or which have a fluidity at ambient temperature include, for example, soybean oil, rape oil, corn oil, sesame oil, cotton seed oil, safflower oil, castor oil, peanut oil, rice germ oil, wheat germ oil, camellia oil, palm oil, olive oil, jojoba oil, macadamia nut oil, avocado oil, castor oil, linseed oil, beefsteak plant oil, eucalyptus oil, evening primrose oil, turtle oil, mink oil, lard, beef tallow, fish oil, liquid paraffin, isoparaffin, vaseline, squalane, squalene, turpentine oil, isopropyl myristate, isopalmityl myristate, 2-octyldodecyl myristate, cetyl 2-ethylhexanoate, glyceryl tri-2-ethylhexanoate, glyceryl tricaprylate, triglyceride of mixed fatty acids of caprylic acid and capric acid, neopentyl glycol di-2-ethylhexanoate, diisostearyl malate, isononyl isonanoate (3,5,5-trimethylhexyl-3',5',5'-trimethylhexanoate), cholesteryl 12-hydroxystearate, monoesters to hexaesters of dipentaerythritol and isostearic acid and/or higher fatty acids (products of Emery Co., Ltd), glyceryl esters of p-methoxysinnamic acid and 2-ethylhexanoic acid, isooctyl p-methoxycinnamate, hardened soybean oil, hardened rape oil, hardened palm oil, hardened fish oil, glyceryl tristearate, rosin, cholesterol, phytosterols (campesterol, stigmasterol, sitosterol, etc.), orange raffinate, lanolin, myristic acid, palmitic acid, isopalmitic acid, stearic acid, isostearic acid (a product of Emery Co., Ltd), oleic acid, linolic acid, linoleic acid, ricinoleic acid, 12-hydroxystearic acid, 10-hydroxystearic acid, behenic acid, erucic acid, arachidonic acid, eicosapentaenoic acid, docosahexaenoic acid, myristyl alcohol, cetyl alcohol, stearyl alcohol, isostearyl alcohol, behenyl alcohol, lanolin alcohol, paraffin wax, microcrystalline wax, ceresine wax, bees wax, vaseline, hard fat, carnauba wax, candelilla wax, rice bran wax, shellac, dimethylpolysiloxane, methylphenylpolysiloxane, and essential oils derived from animals and vegetables. These oily components may be used either alone or in combination of two or more of them.

The emulsifier content of the oil phase of the oily composition of the present invention is preferably 0.5 to 50% by weight, more preferably 1 to 30% by weight.

The oil phase of the oily composition of the present invention may contain known additives such as an antiseptic, a colorant and a flavor. When the oily composition contains additives, the amount of them is prefrably 0.01 to 3% by weight based on the whole oil phase of the composition.

The oily composition of the present invention may contain an oil-soluble effective substance in the oil phase. The effective substances include, for example, antioxidants, nutrients, medicines and animal and vegetable extracts. In particular, they include mixed tocopherols, dl-α-tocophenol, acetic acid-dl-α-tocophenol, β-carotene, vitamin A, vitamin D's, vitamin K's, essential fatty acids, γ-oryzanol and Japanese chirate extract. These oil-soluble effective substances may be used either alone or in combination of two or more of them.

When these oil-soluble effective substances are contained in the oil phase, the amount thereof is preferably 0.1 to 99% by weight, more preferably 0.2 to 40% by weight, based on the whole oil phase.

The oily composition of the present invention preferably comprises 0.5 to 70% by weight of the solid phase and 99.5 to 30% by weight of the oil phase.

The oily composition of the present invention has a total water content of not higher than 20% by weight, preferably 0 to 10%, more preferably 0 to 5% and most preferably 0 to 3% by weight. The method for controlling the total water content of the oily composition of the present invention to not higher than 20% by weight is not particularly limited, and it may be a reduced pressure drying method, heat drying method, film distillation drying method, freeze-drying method or the like.

The method for producing the oily composition of the present invention is not particularly limited. It can be produced by, for example, a method which will be described below.

The oily composition of the present invention may be used as it is or after diluting it with an oily component or an organic solvent such as ethanol or xylene for the preparation of foods, feeds, cosmetics, industrial products and medicines. When the oily composition is diluted with the organic solvent, dilution ratio is preferably 0.01 to 10000 parts of the organic solvent for 1 part of the oily composition, more preferably 0.1 to 1000 parts of the organic solvent for 1 part of the oily composition. When the oily component used for the dilution is a hardened oil or wax which is in the solid form at ambient temperature, the obtained product can be in the form of a solid, granules or a powder even when the oily composition of the present invention is in the liquid form at ambient temperature. The solid, granular or powdery product can be obtained also by previously incorporating a solid fat, hardened oil, wax or the like into the oily component of the oily composition of the present invention. Since the oily composition of the present invention scarcely contains water, this composition can be fed into a well-known capsule (such as a gelatin capsule or agar capsule).

Although the effective substances were incorporated into the foods, feeds, cosmetics, industrial products or medicines separately from the oily effective substances in the prior art, both of them can be incorporated into the oily composition of the present invention.

Further, by adding the oily composition of the present invention to an oil or fat, a homogeneous dispersion of the effective substance in the oily substance can be obtained. Unlike a water-in-oil emulsion wherein an aqueous solution or gel is dispersed in an oil phase, the oily composition of the present invention is free from the separation of water or the effective substance during the storage. In addition, since the aqueous substance is not brought into contact with water or the open air, the effective substance can be kept from deterioration, decomposition, rot, etc.

When a person eats the oily composition of the invention containing the aqueous effective substance which have sour, bitter or astringent taste etc., the person can feel no taste, so that the oily composition of the invention can mask the taste of the effective substance by adding the composition into the feeds and medicines or the like.

The description will be made on the process for producing the oily composition of the present invention.

The process for producing the oily composition of the present invention comprises heating an aqueous phase comprising an effective substance selected from the group consisting of a water-soluble substance and water-dispersible substance, an ingredient selected from the group consisting of gelatin and gum arabic, and water to a dissolution temperature of the ingredient or higher, mixing the aqueous phase with an oil phase containing an oily component and an emulsifier to finally obtain a W/O-type emulsion and then dehydrating the emulsion to control the water content of the whole composition at 20% by weight or lower.

The effective substance and the ingredient, oily component and emulsifier to be used are those contained in the oily composition of the present invention.

The water which is not particularly limited is purified water, distilled water, city water or the like. The water may contain an alcohol. The alcohol include, for example, monohydric alcohol such as ethanol and methanol. In this case, the content of the alcohol is preferably 1 to 300 parts by weight for 100 parts by weight of the water.

In the process of the present invention for producing the oily composition, the effective substance and the ingredient are mixed with water to obtain the aqueous phase. The relative amount of the ingredient in the aqueous phase is preferably 0.05 to 60% by weight, more preferably 1 to 40% by weight, based on the whole aqueous phase. The aqueous phase may further contain a polyhydric alcohol and other additives which can be contained in the aqueous phase of the oily composition of the present invention.

Then the aqueous phase is heated to the dissolution temperature of gelatin and/or gum arabic or higher, preferably 1 to 90° C., to make the aqueous solution in molten state.

Separately, the emulsifier and oily component are mixed together to obtain the oil phase. The relative amount of the emulsifier in the oil phase is preferably 0.5 to 50% by weight, more preferably 1 to 30% by weight, based on the whole oil phase. The oil phase may further contain an oily effective substance and other additives which can be contained in the oil phase of the oily composition of the present invention.

Then the oil phase is mixed with the aqueous phase to finally obtain the W/O-type emulsion. In this step, the oil phase is heated to a temperature higher than the heating temperature of the aqueous phase. By thus heating the oil phase, it becomes possible to add an oily component which is in solid state at ambient temperature. The mixing ratio of the aqueous phase to the oil phase (parts by weight of the aqueous phase/parts by weight of the oil phase) is preferably 95/5 to 1/99, more preferably 85/15 to 5/95. The method for finally obtaining the W/O-type emulsion from the mixture of the aqueous phase and oil phase can be selected from known, ordinary methods without any particular limitation. For example, the mixture of the aqueous phase and the oil phase is emulsified with an emulsifying machine such as a propeller, homomixer, homo disper, high-pressure homogenizer or microfluidizer.

Then the W/O type emulsion is dehydrated to a total water content of 20% by weight or below, preferably 0 to 10% by weight, more preferably 0 to 5% by weight and most preferably 0 to 3% by weight to obtain the oily composition.

The method for controlling the total water content of the W/O-type emulsion to not higher than 20% by weight is not particularly limited, and it may be a reduced pressure drying method, heat drying method, film distillation drying method, freeze-drying method or the like. The dehydration treatment may be conducted while the W/O-type emulsion is kept heated or after this emulsion is cooled to room temperature.

The following Examples will further illustrate the present invention, which by no means limit the invention.

In the following Examples, the water content of the oily composition, water content of the solid phase and average particle diameter in the solid phase were determined and calculated by methods described below.

[Water content of oily composition]

About 2 g of the oily composition and about 20 g of sea sand were homogeneously mixed together. The resultant mixture was dried at 105° C. for 2 hours. The water content was determined from the reduction in weight.

[Water content of solid phase]

Since water in the oily composition is contained only in the solid phase, water content of the solid phase was calculated from the water content determined in the above-described item of [Water content of oily composition] according to the following calculation formula:

water content (wt. %) of solid phase=water content of oily composition/(water content of oily composition+weight of solid phase except for water) x 100

[Average particle diameter in solid phase]

The average particle diameter in the solid phase of the oily composition was determined with a laser diffraction-type particle size distribution meter (LA-500; a product of Houiba, Ltd.).

EXAMPLE 1

A solution obtained by mixing 6 g of citric acid, 10 g of gelatin (Gelatin AU-S; a product of Miyagi Kagaku Kogyo Co., Ltd.) and 39 g of water at 60° C. was used as the aqueous phase. Another solution obtained by mixing 40 g of soybean oil and 5 g of hexaglycerol condensed licinoleate (POEMU PR-300, HLB: 1.7) at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated with an oil pump under reduced pressure to obtain the oily composition of the present invention. The obtained oily composition had a water content of 0. 3% by weight, the water content of the solid phase was 1.1% by weight, and the average diameter of the fine solid particles dispersed in the oil phase (hereinafter referred to as "fine solid particles") was 0.8 $\mu$m.

The storability of the oily composition thus obtained was evaluated to obtain the results shown in Table 1.

[Storability of oily composition]

After the oily composition obtained as described above was kept in a constant temperature bath at 5° C. or 40° C. for one month, three months and six months, the appearance of the oily composition was macroscopically observed. In addition, after the oily composition was kept at room temperature for one month, three months and six months, the appearance of the oily composition was also macroscopically observed. The storability at low temperature was also evaluated by the following method: the oily composition was left to stand in a quick freezer at −30° C. for 24 hours and then kept in a refrigerator in which the temperature was kept at −20° C. After storing the oily composition in the refrigerator for 6 months, the temperature thereof was elevated to 25° C., and the appearance thereof was macroscopically observed according to the following criteria to obtain the results shown in Table 1 together with the results of the macroscopic observation conducted immediately after the prodouction:

⊚: No abnormality was found at all in the oily composition.

○: The oil phase separation was found in less than 5% by weight of the whole composition.

Δ: The oil phase separation was found in at least 5% by weight of the whole composition.

□: The separation of water was found.

x: Precipitates were found.

▲: The oily composition was colored deep yellow.

■: The oily composition became moldy.

EXAMPLE 2

A solution obtained by mixing 6 g of common salt, 5 g of gelatin (Gelatin A-U; a product of Miyagi Kagaku Kogyo Co., Ltd.), 5 g of D-sorbitol solution (Sorbit L-70; a product of Towa Kasei Kogyo Co.; water content: 30% by weight) and 38 g of water at 60° C. was used as the aqueous phase. Another solution obtained by mixing 40 g of soybean oil, 4 g of POEMU PR-300 and 2 g of lecithin (Lecithin DX; a product of The Nisshin Oil Mills, Ltd.) at 60° C. was used as the oil phase. After the same procedure as that of Example 1 was repeated, the oily composition of the present invention was obtained. The obtained oily composition had a water content of 7.3% by weight, the water content of the solid phase was 24.7% by weight, and the average diameter of the fine solid particles dispersed in the oil phase (hereinafter referred to as "fine solid particles") was 1.3 $\mu$m. The storability of the oily composition thus obtained was evaluated in the same manner as that of Example 1 to obtain the results shown in Table 1.

EXAMPLE 3

A solution obtained by mixing 1 g of sodium L-glutamate, 3 g of gelatin (Gelatin AP-250; a product of Nitta Gelatin Inc.), 0.1 g of guar gum (BISUTOPPU B-20; a product of SANEIGEN F.F.I. Co., Ltd.) and 48.4 g of water at 60° C. was used as the aqueous phase. Another solution obtained by mixing 25 g of soybean oil, 18 g of oleic acid diglyceride and 4.5 g of hexaglycerol condensed licinoleate (SY GURISUTA CR-500; a product of Sakamoto Yakuhin Industry Co., Ltd.; HLB: 2) at 60° C. was used as the oil phase. The aqueous phase was slowly added to the oil phase while they were mixed and emulsified with a homomixer at 6,000 rpm and at 60° C. for 20 minutes, and then the emulsion was further emulsified with a high-pressure homogenizer under a pressure of 500 kg/cm2 to obtain a W/O-type emulsion. Then this emulsion was dehydrated with an oil pump under reduced pressure to obtain the oily composition of the present invention. The obtained oily composition had a water content of 1.6% by weight, the water content of the solid phase was 17.0% by weight, and the average diameter of the fine solid particles was 1.1 $\mu$m. The storability of the oily composition thus obtained was evaluated in the same manner as that of Example 1 to obtain the results shown in Table 1.

EXAMPLE 4

A solution obtained by mixing 1 g of sodium L-ascorbate, 3 g of Gelatin AP-250, 0.1 g of agar (Ina Kanten S-7; a product of Ina Shokuhin Kogyo Co., Ltd.) and 48.4 g of water at 60° C. was used as the aqueous phase. Another solution obtained by mixing 25 g of soybean oil, 18 g of oleic acid diglyceride and 4.5 g of SY GURISUTA CR-500 at 60° C. was used as the oil phase. The aqueous phase was slowly added to the oil phase while they were mixed and emulsified with a homomixer at 6,000 rpm and at 60° C. for 20 minutes, and then the emulsion was further emulsified with a high-pressure homogenizer under a pressure of 200 kg/cm2 to obtain a W/O-type emulsion. Then this emulsion was dehydrated with an oil pump to obtain the oily composition of the present invention. The obtained oily composition had a water content of 0.3% by weight, the water content of the solid phase was 3.6% by weight, and the average diameter of the fine solid particles was 0.3 $\mu$m. The storability of the oily composition thus obtained was evaluated in the same manner as that of Example 1 to obtain the results shown in Table 1.

EXAMPLE 5

A solution obtained by mixing 10 g of L-ascorbic acid, 17 g of gelatin (Gelatin MJ; a product of Nitta Gelatin Inc.), 1 g of lecithin obtained by enzymatic degradation (BASIS LG-10K; a product of The Nisshin Oil Mills, Ltd.) and 39.8 g of water at 60° C. was used as the aqueous phase. Another solution obtained by mixing 25 g of soybean oil, 0.2 g of β-carotene, 5 g of tetraglycerol tristearate (SY GURISUTA TS-310; a product of Sakamoto Yakuhin Industry Co., Ltd.; HLB: 4) and 2 g of a glycerol monofatty acid ester (EMARUJI MU, a product of Riken Vitamin Co., Ltd.; HLB: 4.2) at 60° C. was used as the oil phase. Then the same procedure as that of Example 1 was repeated to obtain the oily composition of the present invention. The obtained oily composition had a water content of 0.4% by weight, the water content of the solid phase was 0.9% by weight, and the average diameter of the fine solid particles was 0.6 $\mu$m. The storability of the oily composition thus obtained was evaluated in the same manner as that of Example 1 to obtain the results shown in Table 1.

EXAMPLE 6

A solution obtained by mixing 10 g of L-ascorbic acid, 17 g of Gelatin MJ, 1 g of BASIS LG-10K and 39.8 g of water at 60° C. was used as the aqueous phase. Another solution obtained by mixing 25 g of soybean oil, 0.2 g of β-carotene, 5 g of SY GURISUTA TS-310 and 2 g of EMARUJI MU at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated with an evaporator to obtain the oily composition of the present invention. The obtained oily composition had a water content of 2.6% by weight, the water content of the solid phase was 5.4% by weight, and the average diameter of the fine solid particles was 1.2 μm. The storability of the oily composition thus obtained was evaluated in the same manner as that of Example 1 to obtain the results shown in Table 1.

EXAMPLE 7

A solution obtained by mixing 0.5 g of Aspirin, 16 g of Gelatin A-U, 5 g of glycerol, 0.2 g of polyoxyethylene (40 mol) sorbitol tetraoleate (REODORU 440; a product of Kao Corporation; HLB: 11.8) and 38.3 g of water at 60° C. was used as the aqueous phase. Another solution obtained by mixing 30 g of liquid paraffin, 1 g of bees wax, 4 g of squalane, 4 g of sorbitol sesquioleate (COSMOL 82; a product of The Nisshin Oil Mills, Ltd.; HLB: 5) and 1 g of polyoxyethylene (5 mol)-hardened castor oil (EMAREKKSU HC-5; a product of NIHON EMARUJONN Co., Ltd.; HLB: 3) at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated by the freeze-drying method obtain the oily composition of the present invention. The obtained oily composition had a water content of 11.2% by weight, the water content of the solid phase was 26.4% by weight, and the average diameter of the fine solid particles was 2.2 μm. The storability of the oily composition thus obtained was evaluated in the same manner as that of Example 1 to obtain the results shown in Table 1.

EXAMPLE 8

A solution obtained by mixing 2 g of vitamin B 1, 15 g of gum arabic (ARABIKKUKORU SS; a product of SANEI YAKUHIN BOUEKI Co., Ltd.), 5 g of reduced starch saccharide (AMAMIRU, a product of TOWA KASEI KOGYOU Co., Ltd.; water content: 30% by weight) and 35 g of water at 60° C. was used as the aqueous phase. Another solution obtained by mixing 15 g of refined fish oil, 15 g of a medium chain length fatty acid tuiglyceride (ODO; a product of The Nisshin Oil Mills, Ltd.), 4 g of POEMU PR-300 and 1 g of a monoester of glycerol and a fatty acid (EMARUJI MS, a product of Riken Vitamin Co., Ltd.; HLB: 4.3) at 60° C. was used as the oil phase. Then the same procedure as that of Example 1 was repeated to obtain the oily composition of the present invention. The obtained oily composition had a water content of 0.2% by weight, the water content of the solid phase was 0.5% by weight, and the average diameter of the fine solid particles was 0.6 μm. The storability of the oily composition thus obtained was evaluated in the same manner as that of Example 1 to obtain the results shown in Table 1.

EXAMPLE 9

A solution obtained by mixing 8 g of calcium chloride, 5 g of Gelatin A-U, 5 g of ARABIKKUKORU SS, 5 g of AMAMIRU and 40.9 g of water at 60° C. was used as the aqueous phase. Another solution obtained by mixing 33 g of soybean oil, 2 g of beef tallow, 0.2 g of ascorbic acid stearate, 0.5 g of EMARUJI MS and monogly citrate (POEMU K-30; a product of Riken Vitamin Co., Ltd.; HLB: 3) at 60° C. was used as the oil phase. Then the same procedure as that of Example 1 was repeated to obtain the oily composition of the present invention. The obtained oily composition had a water content of 12.1% by weight, the water content of the solid phase was 26.9% by weight, and the average diameter of the fine solid particles was 1.5 μm. The storability of the oily composition thus obtained was evaluated in the same manner as that of Example I to obtain the results shown in Table 1.

EXAMPLE 10

A solution obtained by mixing 1 g of citric acid, 3 g of Gelatin A-U and 51 g of water at 60° C. was used as the aqueous phase. Another solution obtained by mixing 40 g of soybean oil and 5 g of POEMU PR-300 at 60° C. was used as the oil phase. Then the same procedure as that of Example 1 was repeated to obtain the oily composition of the present invention. The obtained oily composition had a water content of 0.2% by weight, the water content of the solid phase was 2.4% by weight, and the average diameter of the fine solid particles was 0.7 μm. The storability of the oily composition thus obtained was evaluated in the same manner as that of Example 1 to obtain the results shown in Table 1.

EXAMPLE 11

A solution obtained by mixing 0.5 g of citric acid, 0.6 g of Gelatin A-U and 53.9 g of water at 60° C. was used as the aqueous phase. Another solution obtained by mixing 40 g of soybean oil and 5 g of POEMU PR-300 at 60° C. was used as the oil phase. Then the same procedure as that of Example 1 was repeated to obtain the oily composition of the present invention. The obtained oily composition had a water content of 0.1% by weight, the water content of the solid phase was 4.0% by weight, and the average diameter of the fine solid particles was 0.4 μm. The storability of the oily composition thus obtained was evaluated in the same manner as that of Example 1 to obtain the results shown in Table 1.

EXAMPLE 12

A solution obtained by mixing 4 g of citric acid, 4 g of ascorbic acid, 10 g of Gelatin A-U and 40 g of water at 60° C. was used as the aqueous phase. Another solution obtained by mixing 35 g of soybean oil and 7 g of POEMU PR-300 at 60° C. was used as the oil phase. Then the same procedure as that of Example 1 was repeated to obtain the oily composition of the present invention. The obtained oily composition had a water content of 8.4% by weight, the water content of the solid phase was 23.4% by weight, and the average diameter of the fine solid particles was 1.9 μm. The storability of the oily composition thus obtained was evaluated in the same manner as that of Example 1 to obtain the results shown in Table 1.

EXAMPLE 13

A solution obtained by mixing 8 g of L-ascorbic acid, 10 g of Gelatin A-U and 40 g of water at 60° C. was used as the aqueous phase. Another solution obtained by mixing 37 g of a mix tocopherol (Tocopherol 100; a product of The Nisshin Oil Mills, Ltd.) and 5 g of POEMU PR-300 at 60° C. was used as the oil phase. Then the same procedure as that of Example 1 was repeated to obtain the oily composition of the present invention. The obtained oily composition had a water content of 1.5% by weight, the water content of the solid phase was 4.8% by weight, and the average diameter of the fine solid particles was 1.1 μm. The storability of the oily composition thus obtained was evaluated in the same manner as that of Example 1 to obtain the results shown in Table 1.

EXAMPLE 14

A solution obtained by mixing 10 g of citric acid, 10 g of L-ascorbic acid, 0.3 g of rosemary extract (RM 21 C; a product of Tokyo Tanabe Co., Ltd.), 0.2 g of tea extract [SANFUDO powder (30%); a product of Sankyo Co., Ltd.], 20 g of Gelatin A-U and 33.5 g of water at 60° C. was used as the aqueous phase. Another solution obtained by mixing 20 g of soybean oil and 6 g of POEMU PR-300 at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated under reduced pressure with an oil pump to obtain the oily composition of the present invention. The obtained oily composition had a water content of 18.7% by weight, the water content of the solid phase was 27.4% by weight, and the average diameter of the fine solid particles was 0.9 μm. The storability of the oily composition thus obtained was evaluated in the same manner as that of Example 1 to obtain the results shown in Table 1.

EXAMPLE 15

A solution obtained by mixing 6 g of calcium chloride, 2 g of casein calcium peptide (CCP; a product of Taiyo Kagaku Co., Ltd.), 15 g of Gelatin A-U and 45 g of water at 60° C. was used as the aqueous phase. Another solution obtained by mixing 26 g of soybean oil and 6 g of POEMU PR-300 at 60° C. was used as the oil phase. Then the same procedure as that of Example 1 was repeated to obtain the oily composition of the present invention. The obtained oily composition had a water content of 12.1% by weight, the water content of the solid phase was 24.8% by weight, and the average diameter of the fine solid particles was 0.8 μm. The storability of the oily composition thus obtained was evaluated in the same manner as that of Example 1 to obtain the results shown in Table 1.

COMPARATIVE EXAMPLE 1

40 g of soybean oil was mixed with 5 g of POEMU PR-300 at 60° C. to obtain a solution. A mixed powder of 10 g of Gelatin AU-S and 6 g of citric acid was added to the solution, and the obtained mixture was stirred (6,000 rpm) with a homomixer to obtain an oily composition. In the oily composition thus obtained, the gelatin was not dissolved but formed an aggregate. The obtained oily composition had a water content of 0.1% by weight, and the water content of the solid phase was 0.4% by weight. The particle diameter could not be determined because of the aggregation. One day after the preparation, the solid was almost completely precipitated and the oil phase was transparent.

COMPARATIVE EXAMPLE 2

A solution obtained from 6 g of citric acid and 39 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated under reduced pressure with an oil pump to obtain the oily composition containing the emulsifier dissolved therein. Citric acid crystals were precipitated in the course of the dehydration. The obtained oily composition had a water content of 3.2% by weight, and the water content of the solid phase was 21.9% by weight. The particle diameter could not be determined because of the aggregation. One day after the preparation, the solid was almost completely precipitated and the oil phase was transparent.

COMPARATIVE EXAMPLE 3

A solution obtained by mixing 6 g of citric acid, 2 g of Gelatin A-U and 39 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated under reduced pressure with an oil pump to obtain the oily composition. Sodium citrate precipitates were formed in the oil phase of the obtained oily composition. This oily composition had a water content of 5.6% by weight, and the water content of the solid phase was 28.2% by weight. The particle diameter could not be determined because of the aggregation. One day after the preparation, the solid was almost completely precipitated and the oil phase was transparent.

COMPARATIVE EXAMPLE 4

A solution obtained by mixing 1 g of citric acid, 3 g of sodium caseinate and 51 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with a homomixer at 6,000 rpm and at 60° C. for 20 minutes to obtain a W/O-type emulsion. Then this emulsion was dehydrated under reduced pressure with an oil pump to obtain the oily composition. Sodium caseinate and citric acid were precipitated in the oil phase of the obtained oily composition. This oily composition had a water content of 0.1% by weight, and the water content of the solid phase was 1.2% by weight. The particle diameter could not be determined because of the aggregation. One day after the preparation, the solid was almost completely precipitated and the oil phase was transparent.

COMPARATIVE EXAMPLE 5

An oily composition was obtained in the same manner as that of Comparative Example 4 except that 3 g of sodium caseinate was replaced with 3 g of dry egg white (Dry Egg White K; a product of Q. P. Corporation). The precipitates of citric acid and egg white were formed in the oil phase in the course of the dehydration. The obtained oily composition had a water content of 2.7% by weight, and the water content of the solid phase was 25.4% by weight. The particle diameter could not be determined because of the aggregation. One day after the preparation, the solid was almost precipitated and the oil phase was transparent.

COMPARATIVE EXAMPLE 6

An oily composition was obtained in the same manner as that of Comparative Example 4 except that 3 g of sodium caseinate was replaced with 3 g of a degradation product of soybean protein (SORUPI 2000; a product of The Nisshin Oil Mills, Ltd.). The precipitates of citric acid and soybean protein were formed in the oil phase in the course of the dehydration. The obtained oily composition had a water content of 0.2% by weight, and the water content of the solid phase was 2.4% by weight. The particle diameter could not be determined because of the aggregation. One day after the preparation, the solid was almost completely precipitated and the oil phase was transparent.

COMPARATIVE EXAMPLE 7

A solution obtained by mixing 0.5 g of citric acid, 0.6 g of BISUTOPPU B-20 and 53.9 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with 20 a homomixer at 6,000 rpm and at 60° C. for 20 minutes to obtain a W/O-type emulsion. Then this emulsion was dehydrated under reduced pressure with an oil pump to obtain the oily composition. Citric acid and guar gum precipitates were formed in the oil phase of the obtained oily composition. This oily composition had a water content of 0.6% by weight, and the water content of the solid phase was 20.2% by weight. The particle diameter could not be determined because of the aggregation. One day after the preparation, the solid was almost completely precipitated and the oil phase was transparent.

COMPARATIVE EXAMPLE 8

An oily composition was obtained in the same manner as that of Comparative Example 6 except that 0.6 g of BISU-TOPPU B-20 was replaced with 0.6 g of xanthane gum (SANNEISU; a product of SANEIGEN F.F.I. Co. Ltd.). The precipitates of xanthane gum were formed in the course of the dehydration. The obtained oily composition had a water content of 0.8% by weight, and the water content of the solid phase was 25.3% by weight. The particle diameter could not be determined because of the aggregation. One day after the preparation, the solid was almost completely precipitated and the oil phase was transparent.

COMPARATIVE EXAMPLE 9

An oily composition was obtained in the same manner as that of Comparative Example 6 except that 0.6 g of BISU-TOPPU B-20 was replaced with 0.6 g of locust bean gum (BISUTOPPU d-30; a product of SANEIGEN F.F. I. Co. Ltd). The precipitates of locust bean gum were formed in the course of the dehydration. The obtained oily composition had a water content of 0.7% by weight, and the water content of the solid phase was 22.8% by weight. The particle diameter could not be determined because of the aggregation. One day after the preparation, the solid was almost completely precipitated and the oil phase was transparent.

COMPARATIVE EXAMPLE 10

An oily composition was obtained in the same manner as that of Comparative Example 6 except that 0.6 g of BISU-TOPPU B-20 was replaced with 0.6 g of carrageenan (carrageenin CSI-1; a product of SANEIGEN F.F.I. Co. Ltd.). The precipitates of carrageenan were formed in the course of the dehydration. The obtained oily composition had a water content of 0.3% by weight, and the water content of the solid phase was 11.2% by weight. The particle diameter could not be determined because of the aggregation. One day after the preparation, the solid was almost completely precipitated and the oil phase was transparent.

COMPARATIVE EXAMPLE 11

An oily composition was obtained in the same manner as that of Comparative Example 6 except that 0.6 g of BISU-TOPPU B-20 was replaced with 0.6 g of Ina Agar S-7. The precipitates of agar were formed in the course of the dehydration. The obtained oily composition had a water content of 0.6% by weight, and the water content of the solid phase was 120.2% by weight. The particle diameter could not be determined because of the aggregation. One day after the preparation, the solid was almost completely precipitated and the oil phase was transparent.

COMPARATIVE EXAMPLE 12

An oily composition was obtained in the same manner as that of Comparative Example 6 except that 0.6 g of BISU-TOPPU B-20 was replaced with 0.6 g of pectin (GENU PECTIN LM-104AS; a product of SANSYOU Co., Ltd.). The precipitates of pectin were formed in the course of the dehydration. The obtained oily composition had a water content of 0.2% by weight, and the water content of the solid phase was 7.7% by weight. The particle diameter could not be determined because of the aggregation. One day after the preparation, the solid was almost completely precipitated and the oil phase was transparent.

COMPARATIVE EXAMPLE 13

An oily composition was obtained in the same manner as that of Comparative Example 6 except that 0.6 g of BISU-TOPPU B-20 was replaced with 0.6 g of alginic acid (DAKKUARUGIN; a procuct of Kibun Food Chemifa Co., Ltd.). The precipitates of alginic acid were formed in the course of the dehydration. The obtained oily composition had a water content of 0.5% by weight, and the water content of the solid phase was 17.4% by weight. The particle diameter could not be determined because of the aggregation. One day after the preparation, the solid was almost completely precipitated and the oil phase was transparent.

COMPARATIVE EXAMPLE 14

An oily composition was obtained in the same manner as that of Comparative Example 6 except that 0.6 g of BISU-TOPPU B-20 was replaced with 0.6 g of Gelan gum (KERUKOGERU; a product of Dainippon Pharmaceutical Co., Ltd.). The precipitates of Gellan gum were formed in the course of the dehydration. The obtained oily composition had a water content of 0.8% by weight, and the water content of the solid phase was 25.3% by weight. The particle diameter could not be determined because of the aggregation. One day after the preparation, the solid was almost completely precipitated and the oil phase was transparent.

COMPARATIVE EXAMPLE 15

A solution obtained by mixing 6 g of citric acid and 39 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with a homomixer at 6,000 rpm and at 60° C. for 20 minutes to obtain a W/O-type emulsion. This oily composition had a water content of 39.0% by weight, and the average diameter of the emulsified particles was 1.8 μm. The storability of the W/O-type emulsion thus obtained was evaluated in the same manner as that of Example 1 to obtain the results shown in Table 2.

COMPARATIVE EXAMPLE 16

A solution obtained by mixing 6 g of citric acid and 39 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with a homomixer at 6,000 rpm and at 60° C. for 20 minutes and then the obtained emulsion was further emulsified with a high-pressure homogenizer under a pressure of 500 kg/cm2 to obtain the W/O-type emulsion. This oily composition had a water content of 39.1% by weight, and the average diameter of the emulsified particles was 0.7 μm. The storability of the W/O-type emulsion thus obtained was evaluated in the same manner as that of Example 1 to obtain the results shown in Table 2.

COMPARATIVE EXAMPLE 17

A W/O-type emulsion was obtained in the same manner as that of Example 14. Then the W/O-type emulsion was dehydrated under reduced pressure with an oil pump for a period of time shorter than that of Example 14 to obtain an oily composition having a water content higher than that in Example 14. The resultant oily composition had a water content of 21.8% by weight, the water content of the solid phase was 31.4% by weight, and the average diameter of the fine solid particles was 1.1 μm. The storability of the obtained oily composition was evaluated in the same manner as that of Example 1 to obtain the results shown in Table 2.

COMPARATIVE EXAMPLE 18

A W/O-type emulsion was obtained in the same manner as that of Example 15. Then the W/O-type emulsion was dehydrated under reduced pressure with an oil pump for a period of time shorter than that of Example 15 to obtain an oily composition having a water content higher than that in Example 15. The resultant oily composition had a water content of 19.1% by weight, the water content of the solid phase was 36.1% by weight, and the average diameter of the fine solid particles was 1.1 μm. The storability of the obtained oily composition was evaluated in the same manner as that of Example 1 to obtain the results shown in Table 2.

COMPARATIVE EXAMPLES 19 to 31

The W/O-type emulsions obtained in Examples 1 to 13 but which were not yet dehydrated were used as the emulsions of Comparative Examples 19 to 31, respectively. The W/O-type emulsions had water contents of 40.1, 40.0, 48.8, 48.6, 41.5, 41.6, 39.8, 37.9, 42.4, 51.1, 53.9, 40.0 and 40.1% by weight, respectively, and average diameter of the emulsified particles of 1.2, 0.8, 0.5, 1.2, 2.2, 2.0, 1.6, 2.6, 2.3, 1.1, 1.6, 2.0 and 1.8 μm, respectively. The storability of each W/O-type emulsion was evaluated in the same manner as that of Example 1 to obtain the results shown in Table 2 (Comparative Examples 19 to 21), Table 3 (Comparative Examples 22 to 26) and Table 4 (Comparative Examples 27 to 31).

COMPARATIVE EXAMPLE 32

A solution obtained by mixing 6 g of citric acid, 10 g of Gelatin AU-S and 39 g of water at 60° C. was used as the aqueous phase. Another solution obtained by mixing 40 g of soybean oil and 5 g of POEMU PR-300 at 60° C. was used as the oil phase. The aqueous phase was slowly added to the oil phase while they were mixed and emulsified with a spatula for 20 minutes. Affter the completion of the emulsification, the obtained product was dehydrated with an oil pump under reduced pressure to obtain an oily composition. This oily composition had a water content of 0.3% by weight, and the average diameter of the fine solid particles was 6.1 μm. One month after the preparation, the solid was almost completely precipitated and the oil phase was transparent.

TABLE 1

| | Examples | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Immediately after preparation | ◉ | ◉ | ◉ | ◉ | ◉ | ◉ | ◉ | ◉ | ◉ | ◉ | ◉ | ◉ | ◉ | ◉ | ◉ |
| 5° C., 1 month | ◉ | ◉ | ◉ | ◉ | ◉ | ◉ | ◉ | ◉ | ◉ | ◉ | ◉ | ◉ | ◉ | ◉ | ◉ |
| 5° C., 3 months | ◉ | ◉ | ◉ | ◉ | ◉ | ◉ | ◉ | ◉ | ◉ | ◉ | ◉ | ◉ | ◉ | ◉ | ◉ |
| 5° C., 6 months | ◉ | ◉ | ◉ | ◉ | ◉ | ◉ | ◉ | ◉ | ◉ | ◉ | ◉ | ◉ | ◉ | ◉ | ◉ |
| Room temp. | | | | | | | | | | | | | | | |
| 1 month | ◉ | ◉ | ◉ | ◉ | ◉ | ◉ | ◉ | ◉ | ◉ | ◉ | ◉ | ◉ | ◉ | ◉ | ◉ |
| 3 months | ◉ | ◉ | ◉ | ◉ | ◉ | ◉ | ◉ | ◉ | ◉ | ◉ | ◉ | ◉ | ◉ | ◉ | ◉ |
| 6 months | ◉ | ◉ | ◉ | ◉ | ◉ | ◉ | ◉ | ◉ | ◉ | ◉ | ◉ | ◉ | ◉ | ◉ | ◉ |
| 40° C., 1 month | ◉ | ◉ | ◉ | ◉ | ◉ | ◉ | ◉ | ◉ | ◉ | ◉ | ◉ | ◉ | ◉ | ◉ | ◉ |
| 40° C., 3 months | ◉ | ◉ | ◉ | ◉ | ◉ | ◉ | ◉ | ◉ | ◉ | ◉ | ◉ | ◉ | ◉ | ◉ | ◉ |
| 40° C., 6 months | ◉ | ◉ | ◉ | ◉ | ◉ | ◉ | ◉ | ◉ | ◉ | ◉ | ◉ | ◉ | ◉ | ○ | ○ |
| Freezing 6 months | ◉ | ◉ | ◉ | ◉ | ◉ | ○ | ◉ | ◉ | ○ | ◉ | ◉ | ◉ | ◉ | ○ | ○ |

TABLE 2

| | Comparative Examples | | | | |
|---|---|---|---|---|---|
| | 17 | 18 | 19 | 20 | 21 |
| Immediately after preparation | ◉ | ◉ | ◉ | ◉ | ◉ |
| 5° C., 1 month | ○□ | ○□ | ○□ | ○□ | ○□ |
| 5° C., 3 months | ○□ | ○□ | ○□ | ○□ | ○□ |
| 5° C., 6 months | ○□ | ○□ | ○□ | ○□ | ○□ |
| Room temp. | | | | | |
| 1 month | ○□ | ○□ | ○□ | ○□ | ○□ |
| 3 months | ○□ | ○□ | ○□■ | ○□■ | ○□■ |
| 6 months | ○□ | ○□ | △□▲■ | △□▲■ | △□▲■ |
| 40° C., 1 month | ○□ | ○□ | △□▲■ | △□▲■ | △□▲■ |
| 40° C., 3 months | ○□ | ○□ | △□▲■ | △□▲■ | △□▲■ |

TABLE 2-continued

| | Comparative Examples | | | | |
|---|---|---|---|---|---|
| | 17 | 18 | 19 | 20 | 21 |
| 40° C., 6 months | ○□▲ | ○□▲ | △□▲■ | △□▲■ | △□▲■ |
| Freezing 6 months | ○□ | ○□ | △□ | △□ | △□ |

TABLE 3

| | Comparative Examples | | | | |
|---|---|---|---|---|---|
| | 22 | 23 | 24 | 25 | 26 |
| Immediately after preparation | ⊙ | ⊙ | ⊙ | ⊙ | ⊙ |
| 5° C., 1 month | ○□ | ○□ | ○□ | ○□ | ○□ |
| 5° C., 3 months | ○□ | ○□▲ | ○□▲ | ○□ | ○□▲ |
| 5° C., 6 months | ○□ | ○□▲ | ○□▲ | ○□ | ○□▲ |
| Room temp. | | | | | |
| 1 month | ○□ | ○□▲ | ○□▲ | ○□ | ○□▲ |
| 3 months | ○□■ | ○□▲■ | ○□▲■ | ○□■ | ○□▲■ |
| 6 months | △□▲■ | △□▲■ | △□▲■ | △□▲■ | △□▲■ |
| 40° C., 1 month | △□▲■ | △□▲■ | △□▲■ | △□▲■ | △□▲■ |
| 40° C., 3 months | △□▲■ | △□▲■ | △□▲■ | △□▲■ | △□▲■ |
| 40° C., 6 months | △□▲■ | △□▲■ | △□▲■ | △□▲■ | △□▲■ |
| Freezing 6 months | △□ | △□ | △□ | △□ | △□ |

TABLE 4

| | Comparative Examples | | | | |
|---|---|---|---|---|---|
| | 27 | 28 | 29 | 30 | 31 |
| Immediately after preparation | ⊙ | ⊙ | ⊙ | ⊙ | ⊙ |
| 5° C., 1 month | ○□ | ○□ | ○□ | ○□ | ○□ |
| 5° C., 3 months | ○□ | ○□ | ○□ | ○□ | ○□ |
| 5° C., 6 months | ○□ | ○□ | ○□ | ○□▲ | ○□▲ |
| Room temp. | | | | | |
| 1 month | ○□ | ○□ | ○□ | ○□▲ | ○□▲ |
| 3 months | ○□■ | ○□■ | ○□■ | △□▲■ | △□▲■ |
| 6 months | △□▲■ | △□▲■ | △□▲■ | △□▲■ | △□▲■ |
| 40° C., 1 month | △□▲■ | △□▲■ | △□▲■ | △□▲■ | △□▲■ |
| 40° C., 3 months | △□▲■ | △□▲■ | △□▲■ | △□▲■ | △□▲■ |
| 40° C., 6 months | △□▲■ | △□▲■ | △□▲■ | △□▲■ | △□▲■ |
| Freezing 6 months | △□ | △□ | △□ | △□ | △□ |

The content of the solid phase in the oily composition (% by weight), the content of the ingredient selected from the group consisting of gelatin and gum arabic for 100 parts by weight of the effective substance (parts by weight), and the content of the ingredient in the solid phase (% by weight) of the oily composition of Examples 1 to 15 and Comparative Examples 1 to 18 were calculated to obtain the results shown in Table 5 (Examples 1 to 15) and Table 6 (Comparative Examples 1 to 18).

TABLE 5

| Example | The content of the solid phase in the oily composition (% by weight) | The content of the ingredient for 100 parts by weight of the effective substance (parts by weight) | The content of the ingredient in the solid phase (% by weight) |
|---|---|---|---|
| 1 | 26.5 | 166.7 | 61.8 |
| 2 | 29.5 | 83.3 | 26.0 |
| 3 | 9.4 | 300.0 | 60.7 |
| 4 | 8.2 | 300.0 | 70.5 |
| 5 | 46.7 | 170.0 | 60.2 |
| 6 | 47.9 | 170.0 | 57.4 |
| 7 | 42.4 | 3200.0 | 54.3 |
| 8 | 37.1 | 300.0 | 63.5 |
| 9 | 45.1 | 125.0 | 33.9 |
| 10 | 8.3 | 300.0 | 73.2 |
| 11 | 2.5 | 120.0 | 52.3 |
| 12 | 35.9 | 125.0 | 42.5 |
| 13 | 31.1 | 125.0 | 52.9 |
| 14 | 68.2 | 100.0 | 35.8 |
| 15 | 48.9 | 187.5 | 49.1 |

TABLE 6

| Comparative Example | The content of the solid phase in the oily composition (% by weight) | The content of the ingredient for 100 parts by weight of the effective substance (parts by weight) | The content of the ingredient in the solid phase (% by weight) |
|---|---|---|---|
| 1 | 26.3 | 166.7 | 62.3 |
| 2 | 14.6 | 0 | 0 |
| 3 | 19.8 | 33.3 | 17.9 |
| 4 | 8.3 | — | — |
| 5 | 10.6 | — | — |
| 6 | 8.3 | — | — |
| 7 | 3.0 | — | — |
| 8 | 3.2 | — | — |
| 9 | 3.1 | — | — |
| 10 | 2.7 | — | — |
| 11 | 3.0 | — | — |
| 12 | 2.6 | — | — |
| 13 | 2.9 | — | — |
| 14 | 3.2 | — | — |
| 15 | — | — | — |
| 16 | — | — | — |
| 17 | 69.4 | 100.0 | 33.9 |
| 18 | 52.9 | 187.5 | 41.7 |

[Masking effect of oily composition]

Twenty normal adults ate the citric acid containing oily compositions of Examples 1, 10, 11 and Comparative Examples 1 to 3 in order to evaluate wheter they felt the taste of citric acid or not. All persons who ate the oily compositions of Examples 1, 10 and 11 did not feel the taste of citric acid, but all person who ate the oily compositions of Comparative Examples 1 to 3 felt the taste of citric acid.

As described above in detail, the oily composition of the present invention, wherein the solid phase having a water content of not higher than 30% by weight is dispersed in the form of fine particles having an average diameter of not larger than 5μm in the oil phase and the whole water content is controlled at not higher than 20% by weight, has an excellent storability, and gelatin and/or gum arabic is not precipitated during the storage for a long period of time.

By the process of the present invention, the oily composition excellent in the storability can be obtained.

Since the oily composition of the present invention is excellent in the storability, it is usable in the fields wherein the storability is demanded such as the fields of foods, feeds, cosmetics, agricultural chemicals and machines.

What is claimed is:

1. An oily composition composed of a solid phase comprising a water-soluble substance and 50 to 4,000 parts by weight, for 100 parts by weight of the water-soluble substance, of an ingredient selected from the group consisting of gelatin and gum arabic, and an oil phase comprising an oily component and an emulsifier, wherein the solid phase in the form of fine particles has an average particle diameter of not larger than 5 µm is dispersed in the oil phase, the water content of the solid phase is not higher than 30% by weight and the water content of the whole composition is not higher than 20% by weight.

2. The oily composition set forth in claim 1, wherein the average particle diameter of the solid phase dispersed in the oil phase is 0.05 to 3 µm.

3. The oily composition set forth in claim 1, wherein the amount of the ingredient in the solid phase is 80 to 2,000 parts by weight, for 100 parts by weight of the effective substance.

4. The oily composition set forth in claim 1, wherein a content of the ingredient in the solid phase is 10 to 99% by weight.

5. The oily composition set forth in claim 1, wherein the emulsifier is a surfactant having an HLB of not higher than 10.

6. The oily composition set forth in claim 1, which contains an oil-soluble effective substance in the oil phase.

7. The oily composition set forth in claim 1, which comprises 0.5 to 70% by weight of the solid phase and 99.5 to 30% by weight of the oil phase.

8. The oily composition set forth in claim 1, wherein the water content of the solid phase is 20% or less by weight.

9. The oily composition set forth in claim 1, wherein the water content of the solid phase is 15% or less by weight.

10. An oily composition composed of a solid phase comprising an effective substance selected from the group consisting of citric acid, common salt, sodium L-glutamate, sodium L-ascorbate, Aspirin, vitamin $B_1$, calcium chloride and casein calcium peptide, and 50 to 4,000 parts by weight, for 100 parts by weight of the effective substance, of an ingredient selected from the group consisting of gelatin and gum arabic, and an oil phase comprising an oily component selected from the group consisting of soybean oil, liquid paraffin, bees wax, squalane and fish oil, beef tallow, and an emulsifier, wherein the solid phase in the form of fine particles having an average particle diameter of 0.05 to 5 µm is dispersed in the oil phase, the water content of the solid phase is 30% or less by weight and the water content of the whole composition is 20% or less by weight.

11. A process for producing an oily composition, which comprises heating an aqueous phase comprising a water-soluble substance, an ingredient selected from the group consisting of gelatin and gum arabic, and water to a dissolution temperature of the ingredient or higher, mixing the aqueous phase with an oil phase containing an oily component and an emulsifier to finally obtain a W/O-type emulsion and then dehydrating the emulsion to control the water content of the whole composition at 20% by weight or lower.

12. The process set fort in claim 11, wherein a relative amount of the ingredient in the aqueous phase is 0.05 to 60% by weight based on the whole aqueous phase.

13. The process set forth in claim 11, wherein the emulsifier is a surfactant having an HLB of not higher than 10.

14. The process set forth in claim 11, wherein relative amounts of the aqueous phase and the oil phase to be mixed are 1 to 95% by weight and 99 to 5% by weight, respectively.

15. The process set forth in claim 11, wherein a content of the ingredient is 0.05 to 60% by weight based on the whole aqueous phase, and a content of the emulsifier is 0.5 to 50% by weight based on the whole oil phase.

16. The process set forth in claim 11, wherein a content of the ingredient is 1 to 40% by weight based on the whole aqueous phase.

17. The process set forth in claim 11, wherein a content of the emulsifier is 1 to 30% by weight based on the whole aqueous phase.

18. The process set forth in claim 11, wherein a mixing weight ratio of the aqueous phase to the oil phase is 95/5 to 1/99.

19. The process set forth in claim 11, wherein a mixing weight ratio of the aqueous phase to the oil phase is 85/15 to 5/95.

20. The process set forth in claim 11, wherein a water content of the whole composition is controlled at 5% or less by weight.

21. The process set forth in claim 11, wherein a water content of the whole composition is controlled at 3% or less by weight.

* * * * *